(12) United States Patent
Wells et al.

(10) Patent No.: US 6,811,966 B2
(45) Date of Patent: *Nov. 2, 2004

(54) METHODS FOR RAPIDLY IDENTIFYING SMALL ORGANIC MOLECULE LIGANDS FOR BINDING TO BIOLOGICAL TARGET MOLECULES

(75) Inventors: Jim Wells, Burlingame, CA (US); Dan Erlanson, San Francisco, CA (US); Andrew C. Braisted, San Francisco, CA (US)

(73) Assignee: Sunesis Pharmaceuticals, Inc., South San Francisco, CA (US)

( * ) Notice: Subject to any disclaimer, the term of this patent is extended or adjusted under 35 U.S.C. 154(b) by 71 days.

This patent is subject to a terminal disclaimer.

(21) Appl. No.: 10/043,833

(22) Filed: Jan. 11, 2002

(65) Prior Publication Data

US 2003/0104471 A1 Jun. 5, 2003

Related U.S. Application Data

(60) Continuation of application No. 09/981,547, filed on Oct. 17, 2001, which is a division of application No. 09/105,372, filed on Jun. 26, 1998, now Pat. No. 6,335,155.

(51) Int. Cl.[7] .......................... C12Q 1/00; G01N 33/53; G01N 24/00
(52) U.S. Cl. .................... 435/4; 435/4; 435/5; 435/7.1; 435/7.5
(58) Field of Search ........................... 435/4, 5, 6, 7.1, 435/7.5, DIG. 2, DIG. 3, DIG. 34, DIG. 22

(56) References Cited

U.S. PATENT DOCUMENTS

| | | | |
|---|---|---|---|
| 5,367,058 A | * 11/1994 | Pitner et al. ............. | 530/391.9 |
| 5,422,281 A | 6/1995 | Harris et al. | |
| 5,571,681 A | 11/1996 | Janda et al. | |
| 5,783,384 A | 7/1998 | Verdine | |
| 5,958,702 A | 9/1999 | Benner | |
| 6,428,956 B1 | * 8/2002 | Crooke et al. ................. | 435/6 |

FOREIGN PATENT DOCUMENTS

| | | |
|---|---|---|
| EP | 0 801 307 | 10/1997 |
| WO | WO 96/13613 | 5/1996 |
| WO | WO 96/27605 | 9/1996 |
| WO | WO 97/43302 | 11/1997 |
| WO | WO 98/11436 | 3/1998 |
| WO | WO 98/11437 | 3/1998 |
| WO | WO 98/25146 | 6/1998 |

OTHER PUBLICATIONS

Loo, J. A. "Studying Noncovalent Protein Complexes by Electrospray Ionization Mass Spectrometry" Mass Spectrometry Reviews, 1997, 16, 1–23.*

Janda, K. D.; Lo, C. –H. L.; Li, T.; Barbas, C. F.; Wirsching, P.; Lerner, R. A. "Direct selection for a catalytic mechanism from combinatorial antibody libraries" PNAS Mar. 1994, 91, 2532–2536.*

Ganem, B.; Li, Y. T.; Henion, J. D. "Detection of noncovalent receptor–ligand complexes by mass spectrometry" Journal of the American Chemical Society 1991, 113(16), 6294–6.*

Przybylski, M.; Glocker, M. O. Angew. Chem. Int. Ed. Engl. 1996, 35, 806–826.*

Wunsch, E.; Spangenberg, R., in Peptides, 1969, E. Schoffone, Ed., North Holland Amsterdam, P. 1971.*

Greene, T. W.; Wuts, P. G. M. in Protective Groups in Organic Synthesis, 1999, John Wiley & Sons, Inc., New York, p. 487.*

Delano, W. L. "Unraveling hot spots in binding interfaces: progress and challenges" Current Opinion in Structural Biology 2002, 12, 14–20.*

Abraham, D.J. et al., "How Allosteric Effectors Can Bind to the Same Protein Residue and Produce Opposite Shifts in the Allosteric Equilibrium" *Biochemistry* 34L150006–15020 (1995).

Boyiri, T. et al., "Bisaldehyde Allosteric Effectors as Molecular Ratchets and Probes" *Biochemistry* 34:15021–15036 (1995).

Bunyapaiboonsri et al., "Dynamic Deconvolution of a Pre–Equilibrated Dynamic Combinatorial Library of Acetylcholinesterase Inhibitors" *ChemBioChem* 2:438–444 (2001).

DeJarias et al., "Use of X–ray Co–crystal Structures and Molecular Modeling to Design Potent and Selective Non–peptide Inhibitors of Cathepsin K" *J. Am. Chem. Soc.* 120(35):9114–9115 (1998).

Erlanson et al., "Site–Directed ligand discovery" *PNAS* 97(17):9367–9372 (Aug. 15, 2000).

Hopkins et al., "Suicide Inhibitor of Cytochrome P450 1A1 and P450 2B1" *Biochem. Pharmacol.* 44(4):787–796 (1992).

(List continued on next page.)

Primary Examiner—Thurman K. Page
Assistant Examiner—Jon D. Epperson
(74) Attorney, Agent, or Firm—Ginger R. Dreger; Heller Ehrman White & McAuliffe LLP

(57) ABSTRACT

The present invention is directed to novel methods for rapidly and unambiguously identifying small organic molecule ligands for binding to biological target molecules. Small organic molecule ligands identified according to the methods of the present invention may find use, for example, as novel therapeutic drug lead compounds, enzyme inhibitors, labeling compounds, diagnostic reagents, affinity reagents for protein purification, and the like. Also presented are novel methods for identifying high affinity binding ligands for a biological target molecule of interest, wherein those methods comprise linking two or more small organic molecule ligands previously identified as being capable of binding to the biological target molecule of interest. Biological target molecules include, for example, polypeptides, nucleic acids, carbohydrates, nucleoproteins, glycoproteins, glycolipids and lipoproteins.

16 Claims, No Drawings

OTHER PUBLICATIONS

Lehn, Jean–Marie, "Dynamic Combinatorial Chemistry and Virtual Combinatorial Libraries" *Chem. Eur. J.* 5(9)2455–2463 (1999).

Mathews et al., "N–Alkylaminobenzotriazoles as Isozyme–Selective Suicide Inhibitors of Rabbit Pulmonary Microsomal Cytochrome P–450" *Mol. Pharmacol.* 39(10):25–32 (1986).

Nicolaou et al., "Combinatorial Synthesis Through Disulfide Exchange: Discovery of Potent Psammaplin A Type Antibacterial Agents Active against Methicillin–Resistant Staphylociccus Aureus (MRSA)" *Chem. Eur. J.* 7(19):4280–4295 (2001).

Nicolaou et al., "Synthesis and Biological Evaluation of Vancomycin Dimers with Potent Activity against VANCOMYCIN–Resistant Bactewria: Target Accelarated Combinatorial Synthesis" *Chem. Eur. J.* 7(17):2824–2843 (2001).

Pollack, S. J. et al., "introduction of Nucelophines and Spectotroscopic Probes into Antibody Combining Sites" *Science* 242:1038–1040 (1998).

Ramstrom and Lehn, "In Situ Generation and Screening of a Dynamic Combinatorial Carbohydrate Library against Concanavalin A" *ChemBioChem* 1:41–48 (2000).

Stanojevic and Verdine, "Deconstruction of GCN4/GCRE into a monomeric peptide–DNA complex" *Nature Structural Biology* 2:450–455 (Jun. 1995).

Woodcroft et al., "N–Aralkylated derivatives of 1–aminobenzotriazole as isozyme–selective mechanism–based inhibitors of guinea pig hepatic cytochrome P–450 dependent monooxygenase activity" *Can J. Physiol. Pharmacol.* 68(9):1278–1285 (1990).

Zhang et al., "Covalent Modification and Active Site–Directed Inactivation of a low Molecular Weight Phosphotyrosyl Protein Phosphatase" *Biochemistry* 31(6):1701–1711 (1992).

* cited by examiner

METHODS FOR RAPIDLY IDENTIFYING SMALL ORGANIC MOLECULE LIGANDS FOR BINDING TO BIOLOGICAL TARGET MOLECULES

This application is a continuation of copending application Ser. No. 09/981,547 filed on Oct. 17, 2001, which is a division of application Ser. No. 09/105,372 filed on Jun. 26, 1998, now U.S. Pat. No. 6,335,155 issued on Jan. 1, 2002.

FIELD OF THE INVENTION

The present invention is directed to novel molecular methods useful for quickly and unambiguously identifying small organic molecule ligands for binding to specific sites on target biological molecules. Small organic molecule ligands identified according to the methods of the present invention find use, for example, as novel therapeutic drug lead compounds, enzyme inhibitors, labeling compounds, diagnostic reagents, affinity reagents for protein purification, and the like.

BACKGROUND OF THE INVENTION

The primary task in the initial phase of generating novel biological effector molecules is to identify and characterize one or more tightly binding ligand(s) for a given biological target molecule. In this regard, many molecular techniques have been developed and are currently being employed for identifying novel ligands that bind to specific sites on biomolecular targets, such as proteins, nucleic acids, carbohydrates, nucleoproteins, glycoproteins and glycolipids. Many of these techniques exploit the inherent advantages of molecular diversity by employing combinatorial libraries of potential ligand compounds in an effort to speed up the identification of functional ligands. For example, combinatorial synthesis of both oligomeric and non-oligomeric libraries of diverse compounds combined with high-throughput screening assays has already provided a useful format for the identification of new lead compounds for binding to chosen molecular targets.

While combinatorial approaches for identifying biological effector molecules have proven useful in certain applications, these approaches also have some significant disadvantages. For example, current synthetic technology is limited in that it allows one to synthesize only a relatively small fraction of the total number of possible library members for any given molecule type. As such, even when appropriate high-throughput screening assays are available for screening a library, only a small fraction of the total number of possible members of any molecule type will be represented in the library and, therefore, -screened for the ability to bind to the chosen target. Thus, combinatorial approaches often do not allow one to identify the "best" ligand for a target molecule of interest.

Additionally, even when appropriate screening assays are available, in many cases techniques which allow identification of the actual library member(s) which bind most effectively to the target are not available or provide ambiguous results, making the actual identification and characterization of functional ligand molecules difficult or impossible. Furthermore, many approaches currently employed to identify novel ligands are dependent upon only a single specific chemistry, thereby limiting the usefulness of such approaches to only a narrow range of applications. Finally, many of the approaches currently employed are expensive and extremely time-consuming. Thus, there is a significant interest in developing new methods which allow rapid, efficient and unambiguous identification of small organic molecule ligands for selected biomolecular targets. It is also desired that such techniques are adaptable to a variety of different chemistries, thereby being useful for a wide range of applications.

Schiff base adduct formation involves the reaction of an available aldehyde or ketone functionality with a primary amine to form an imine-bonded complex. While the Schiff base adduct is relatively unstable, numerous groups have employed aldehyde or ketone compounds for bonding to primary amine functionalities on proteins of interest for a Variety of purposes (see, e.g., Pollack et al., *Science* 242:1038–1040 (1988), Abraham et al., *Biochemistry* 34:15006–15020 (1995) and Boyiri et al., *Biochemistry* 34:15021–15036 (1995)). We herein describe novel techniques useful for rapidly and efficiently identifying organic molecule ligands that bind to specific sites on biomolecular targets, wherein those techniques are adaptable to a variety of different chemistries, preferably Schiff base adduct formation between a target polypeptide and one or more members of a library of potential organic molecule ligands. These methods allow one to unambiguously identify and characterize the organic molecule ligand that binds most efficiently to the chosen target. Additionally, the herein described methods are quick, easy to perform and inexpensive as compared to other currently employed methods.

SUMMARY OF THE INVENTION

Applicants herein describe a molecular approach for rapidly and efficiently identifying small organic molecule ligands that are capable of interacting with and binding to specific sites on biological target molecules, wherein ligand compounds identified by the subject methods may find use, for example, as new small molecule drug leads, enzyme inhibitors, labeling compounds, diagnostic reagents, affinity reagents for protein purification, and the like. The herein described approaches allow one to quickly screen a library of small organic compounds to unambiguously identify those that have affinity for a particular site on a biomolecular target. Those exhibiting affinity for interacting with a particular site are capable of forming a covalent bond with a chemically reactive group at that site, whereby small organic compounds capable of covalent bond formation may be readily identified and characterized. Such methods may be performed quickly, easily and inexpensively and provide for unambiguous results. The small organic molecule ligands identified by the methods described herein may themselves be employed for numerous applications, or may be coupled together in a variety of different combinations using one or more linker elements to provide novel binding molecules.

With regard to the above, one embodiment of the present invention is directed to a method for identifying an organic molecule ligand that binds to a site of interest on a biological target molecule, wherein the method comprises:

(a) obtaining a biological target molecule that comprises or has been modified to comprise a chemically reactive group, wherein the site of interest on the target molecule comprises the chemically reactive group;

(b) combining the target molecule with one or more members of a library of organic compounds that are capable of covalently bonding to the chemically reactive group, wherein at least one member of the library binds to the site of interest to form a covalent bond with the chemically reactive group to form a target molecule/organic compound conjugate; and (c) identifying the organic compound that forms a covalent bond with the chemically reactive group.

In particular embodiments, the biological target molecule is a polypeptide, a nucleic acid, a carbohydrate, a nucleoprotein, a glycopeptide or a glycolipid, preferably a polypeptide, which may be, for example, an enzyme, a hormone, a transcription factor, a receptor, a ligand for a receptor, a growth factor, an immunoglobulin, a steroid receptor, a nuclear protein, a signal transduction component, an allosteric enzyme regulator, and the like. The target molecule may comprise the chemically reactive group without prior modification of the target molecule or may be modified to comprise the chemically reactive group, for example, when a compound comprising the chemically reactive group is bound to the target molecule.

Other embodiments of the above described methods employ libraries of organic compounds which comprise aldehydes, ketones, oximes, hydrazones, semicarbazones, carbazides, primary amines, secondary amines, tertiary amines, N-substituted hydrazines, hydrazides, alcohols, ethers, thiols, thioethers, thioesters, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds and/or acid chlorides, preferably aldehydes, ketones, primary amines, secondary amines, alcohols, thioesters, disulfides, carboxylic acids, acetals, anilines, diols, amino alcohols and/or epoxides, most preferably aldehydes, ketones, primary amines, secondary amines and/or disulfides.

Methods for identifying the organic compound that forms a covalent bond with the chemically reactive group on the target molecule may optionally include processes that employ mass spectrometry, high performance liquid chromatography and/or fragmenting the target protein/organic compound conjugate into two or more fragments.

A particularly preferred embodiment of the present invention is directed to a method for identifying an organic molecule ligand that binds to a biological target molecule of interest, wherein the method comprises:

(a) obtaining a biological target molecule that comprises or has been modified to comprise a first reactive functionality, (b) reacting the target molecule with a compound that comprises (1) a second reactive functionality and (2) a chemically reactive group, wherein the second reactive functionality reacts with the first reactive functionality of the target molecule to form a covalent bond, thereby providing a target molecule comprising the chemically reactive group linked to the target molecule through a covalent bond;

(c) combining the target molecule with one or more members of a library of organic compounds that are capable of covalently bonding to the chemically reactive group, wherein at least one member of the library forms a covalent bond with the chemically reactive group to form a target molecule/organic compound conjugate; and (d) identifying the organic compound that forms a covalent bond with the chemically reactive group.

Preferably, the covalent bond formed from reaction of the first and second reactive functionalities is a disulfide bond formed between two thiol groups and optionally, subsequent to step (c) and prior to step (d) one may liberate the covalently-bonded organic compounds from the conjugate by treatment with an agent that disrupts the disulfide bond, wherein that agent may comprise, for example, dithiothreitol, dithioerythritol, β-mercaptoethanol, sodium borohydride or a phosphine, such as tris-(2-carboxyethyl)-phosphine (TCEP). In various embodiments, the biological target molecule is as described above, preferably a polypeptide that may be obtained, for example, as a recombinant expression product or synthetically The thiol group and thiol functionality may be masked or activated In particularly preferred embodiments, the chemically reactive group is a primary or secondary amine group and the library of organic compounds comprises aldehydes and/or ketones, preferably aldehydes, or the chemically reactive group is an aldehyde or ketone group, preferably an aldehyde, and the library of organic compounds comprises primary and/or secondary amines, thereby allowing Schiff base adduct formation between the chemically reactive group and members of the library. Subsequent to Schiff base adduct formation but prior to identifying the covalently-bound organic compound, a reducing agent may optionally be employed to reduce the imine bond of the Schiff base adduct.

Yet another embodiment of the present invention is directed to a method for identifying a ligand that binds to a biological target molecule of interest, wherein the method comprises:

(a) identifying a first organic molecule ligand that binds to the biological target molecule by at least one of the methods described above;

(b) identifying a second organic molecule ligand that binds to the biological target molecule by at least one of the methods described above; and (c) linking the first and second identified organic molecule ligands through a linker element to form a conjugate molecule that binds to the target molecule.

Preferably, the biological target molecule is a polypeptide. In certain embodiments, the first and second organic molecule ligands may bind to the same site on the target molecule or to different sites thereon. The first and second organic molecule ligands may also be from the same or from different chemical classes.

Additional embodiments of the present invention will become evident to the ordinarily skilled artisan upon review of the present specification.

DETAILED DESCRIPTION OF THE INVENTION

The present invention provides a rapid and efficient method for identifying small organic molecule ligands that are capable of binding to selected sites on biological target molecules of interest. The organic molecule ligands themselves identified by the subject methods find use, for example, as lead compounds for the development of novel therapeutic drugs, enzyme inhibitors, labeling compounds, diagnostic reagents, affinity reagents for protein purification, and the like, or two or more of the identified organic molecule ligands may be coupled together through one or more linker elements to provide novel biomolecule-binding conjugate molecules.

One embodiment of the subject invention is directed to a method for identifying an organic molecule ligand that binds to a site of interest on a biological target molecule. As an initial step in the herein described method, a biological target molecule is obtained as a target for binding to the small organic molecule ligands screened during the process. Biological target molecules that find use in the present invention include all biological molecules to which a small organic molecule may bind and preferably include, for example, polypeptides, nucleic acids, including both DNA and RNA, carbohydrates, nucleoproteins, glycoproteins, glycolipids, and the like. The biological target molecules that find use herein may be obtained in a variety of ways, including but not limited to commercially, synthetically, recombinantly, from purification from a natural source of the biological target molecule, etc.

In a particularly preferred embodiment, the biological target molecule is a polypeptide. Polypeptides that find use herein as targets for binding to organic molecule ligands include virtually any peptide or protein that comprises two or more amino acids and which possesses or is capable of being modified to possess a chemically reactive group for binding to a small organic molecule. Polypeptides of interest finding use herein may be obtained commercially, recombinantly, synthetically, by purification from a natural source, or otherwise and, for the most part are proteins, particularly proteins associated with a specific human disease condition, such as cell surface and soluble receptor proteins, such as lymphocyte cell surface receptors, enzymes, such as proteases and thymidylate synthetase, steroid receptors, nuclear proteins, allosteric enzyme inhibitors, clotting factors, serine/threonine kinases and dephosphorylases, threonine kinases and dephosphorylases, bacterial enzymes, fungal enzymes and viral enzymes, signal transduction molecules, transcription factors, proteins associated with DNA and/or RNA synthesis or degradation, immunoglobulins, hormones, receptors for various cytokines including, for example, erythropoietin/EPO, granulocyte colony stimulating receptor, granulocyte macrophage colony stimulating receptor, thrombopoietin (TPO), IL-2, IL-3, IL-4, IL-5, IL-6, IL-10, IL-11, IL-12, growth hormone, prolactin, human placental lactogen (LPL), CNTF, octostatin, various chemokines and their receptors such as RANTES, MIP1-α, IL-8, various ligands and receptors for tyrosine kinase such as insulin, insulin-like growth factor 1 (IGF-1), epidermal growth factor (EGF), heregulin-α and heregulin-β, vascular endothelial growth factor (VEGF), placental growth factor (PLGF), tissue growth factors (TGF-α and TGF-β), other hormones and receptors such as bone morphogenic factors, folical stimulating hormone (FSH), and leutinizing hormone (LH), tissue necrosis factor (TNF), apoptosis factor-1 and -2 (AP-1 and AP-2), mdm2, and proteins and receptors that share 20% or more sequence identity to these.

The biological target molecule of interest will be chosen such that it possesses or is modified to possess a chemically reactive group which is capable of forming a covalent bond with members of a library of small organic molecules. For example, many biological target molecules naturally possess chemically reactive groups (for example, amine groups, thiol groups, aldehyde groups, ketone groups, alcohol groups and a host of other chemically reactive groups; see below) to which members of an organic molecule library may interact and covalently bond. In this regard, it is noted that polypeptides often have amino acids with chemically reactive side chains (e.g., cysteine, lysine, arginine, and the like). Additionally, synthetic technology presently allows the synthesis of biological target molecules using, for example, automated peptide or nucleic acid synthesizers, which possess chemically reactive groups at predetermined sites of interest. As such, a chemically reactive group may be synthetically introduced into the biological target molecule during automated synthesis.

Moreover, techniques well known in the art are available for modifying biological target molecules such that they possess a chemically reactive group at a site of interest which is capable of forming a covalent bond with a small organic molecule. In this regard, different biological molecules may be chemically modified (using a variety of commercially or otherwise available chemical reagents) or otherwise coupled, either covalently or non-covalently, to a compound that comprises both a group capable of linking to a site on the target molecule and a chemically reactive group such that the modified biological target molecule now possesses an available chemically reactive group at a site of interest. With regard to the latter, techniques for linking a compound comprising a chemically reactive group to a target biomolecule are well known in the art and may be routinely employed herein to obtain a modified biological target molecule which comprises a chemically reactive group at a site of interest.

In one particular embodiment of the present invention, a target molecule comprises at least a first reactive group which, if the target is a polypeptide, may or may not be associated with a cysteine residue of that polypeptide, preferably is associated with a cysteine residue of the polypeptide of interest. Preferably, the polypeptide of interest when initially obtained or subsequently modified comprises only a limited number of free thiol groups which may potentially serve as covalent binding sites for a compound comprising a thiol functionality, where in certain embodiments the polypeptide of interest comprises or has been modified to comprise no more than about 5 free thiol groups, more preferably no more than about 2 free thiol groups, most preferably no more than one free thiol group, although polypeptides of interest having more free thiol groups will also find use. The polypeptide of interest may be initially obtained or selected such that it already possesses the desired number of free thiol groups or may be modified to possess the desired number of free thiol groups. With regard to the latter, "modified to possess" means that the initially selected polypeptide of interest has been recombinantly, chemically, or otherwise altered such that it possesses a different number of free thiol groups than when initially obtained.

Those skilled in the art are well aware of various recombinant, chemical, synthetic, or other techniques that can routinely be employed to modify a polypeptide of interest such that it possess a different number of free thiol groups that are available for covalent bonding to a subsequently-added compound comprising a free thiol group. Such techniques include, for example, site-directed mutagenesis, where a nucleic acid molecule encoding the polypeptide of interest may be altered such that it encodes a polypeptide with a different number of cysteine residues (see, e.g., Gloss et al., *Biochemistry* 31:32–39 (1992)). Site-directed (site-specific) mutagenesis allows the production of variants of an initially obtained polypeptide of interest through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the techniques of site-directed mutagenesis are well known in the art, as exemplified by publications such as Edelman et al., *DNA* 2:183 (1983). As will be appreciated, the site-directed mutagenesis technique typically employs a phage vector that exists in both a single-stranded and double-stranded form.

Typical vectors useful in site-directed mutagenesis include vectors such as the M13 phage, for example, as disclosed by Messing et al., *Third Cleveland Symposium on Macromolecules and Recombinant DNA*, A. Walton, ed., Elsevier, Amsterdam (1981). This and other phage vectors are commercially available and their use is well known to those skilled in the art. A versatile and efficient procedure for the construction of oligodeoxyribonucleotide directed site-specific mutations in DNA fragments using M13-derived vectors was published-by Zoller et al., *Nucleic Acids Res.* 10:6487–6500 (1982)). Also, plasmid vectors that contain a single-stranded phage origin of replication (Veira et al., *Meth. Enzymol.* 153:3 (1987)) may be employed to obtain single-stranded DNA. Alternatively, nucleotide substitutions are introduced by synthesizing the appropriate DNA fragment in vitro, and amplifying it by PCR procedures known in the art.

The PCR technique may also be used in modifying a polypeptide of interest such that it contains a different number of cysteine residues than when initially selected. In a specific non-limiting example of PCR mutagenesis, template plasmid DNA encoding the polypeptide of interest (1 $\mu$g) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and is included in the GENEAMP® kits (obtained from Perkin-Elmer Cetus, Norwalk, Conn. and Emeryville, Calif.), and 25 pmole of each oligonucleotide primer, to a final volume of 50 $\mu$l. The reaction mixture is overlayered with 35 $\mu$l mineral oil. The reaction is denatured for 5 minutes at 100° C., placed briefly on ice, and then 1 $\mu$l *Thermus aquaticus* (Taq) DNA polymerase (5 units/$\mu$l), purchased from Perkin-Elmer Cetus, Norwalk, Conn. and Emeryville, Calif.) is added below the mineral oil layer The reaction mixture is then inserted into a DNA Thermal Cycler (purchased from Perkin-Elmer Cetus) which may be programmed as follows:

2 min. 55° C., 30 sec. 72° C., then 19 cycles of the following:

30 sec. 94° C., 30 sec. 55° C., and 30 sec. 72° C.

At the end of the program, the reaction vial is removed from the thermal cycler and the aqueous phase transferred to a new vial, extracted with phenol/chloroform (50:50 vol), and ethanol precipitated, and the DNA is recovered by standard procedures. This material is subsequently subjected to appropriate treatments for insertion into a vector and expression of the encoded modified polypeptide.

Other methods for modifying a polypeptide of interest so that it contains a different number of cysteine residues that when originally selected include cassette mutagenesis which is based on the technique described by Wells et al., *Gene* 34:315 (1985) and phagemid display, for example, as described in U.S. Pat. No. 4,946,778.

Further details of the foregoing and similar mutagenesis techniques are found in general textbooks, such as, for example, Sambrook et al., *Molecular Cloning: A Laboratory Manual* (New York: Cold Spring Harbor Laboratory Press, 1989) and Ausubel et al., *Current Protocols in Molecular Biology*, Greene Publishing Associates and Wiley-Interscience 1991.

In the particular embodiment which employs a biological target molecule comprising a first reactive functionality, one may directly screen a library of organic molecules that are capable of forming a covalent bond with that first reactive functionality or may covalently bond a compound to that first reactive functionality which comprises the chemically reactive group of interest. With regard to the latter, the target molecule comprising the first reactive functionality may be reacted with a compound that comprises (1) a second reactive functionality and (2) a chemically reactive group, wherein that compound becomes covalently bound to the polypeptide of interest. Specifically, the second reactive functionality of the compound reacts with the first reactive functionality of the target of interest to form a covalent bond, thereby providing a modified target of interest. Preferably, the first and second reactive functionalities are thiol groups, preferably activated thiol groups, that react to form a covalent bond. The target of interest is "modified" in that it now has covalently bound thereto through a covalent bond the compound that comprises the chemically reactive group. Reaction conditions useful for covalently bonding the compound to the target of interest through a covalent bond are known to those skilled in the art and may employ activating groups such as thiopyridine, thionitrobenzoate, and the like.

The compound that comprises the chemically reactive group may also be covalently bound to the target biomolecule through a covalent bond other than a disulfide bond as described above. Those of skill in the art will be capable of covalently linking a chemically reactive group-containing compound to a target biomolecule through virtually any type of covalent bond, including the disulfide bond as described above. In this regard, the first and second reactive functionalities may be any chemically reactive functionalities that are capable of reacting to form a covalent bond. The reaction between the first and second reactive functionalities to form a covalent bond may be the same or different than the reaction between the chemically reactive group and library member to form a covalent bond (see below).

For the most part, the compound that bonds to the target biomolecule of interest through a covalent, preferably disulfide bond will be relatively small, preferably comprising less than about 20, more preferably less than about 10, most preferably less than about 5 carbon atoms, although compounds with more carbon atoms may also find use herein. Such compounds will also possess a thiol functionality capable of forming a covalent bond with the free thiol group of the biological target molecule and may also possess other heteroatoms at certain sites within the compound. A particularly preferred compound for use in this embodiment of the invention is thioethylamine or a derivative thereof, such as 2-amino ethanethiol, which is capable of forming a disulfide bond with the free thiol group of the biological target molecule as well as providing a chemically reactive amine group for bonding to members of a library of organic molecules.

The "chemically reactive group" that is either naturally or otherwise possessed by the biological target molecule or becomes part of the target molecule after modification thereof as described above may be any of a number of different chemically reactive groups and is chosen so as to be compatible with the library of organic molecule compounds that will subsequently be screened for bonding at that site. Specifically, the chemically reactive group provides a site at which covalent bond formation between the chemically reactive group and a member of the library of organic compounds may occur. Thus, the chemically reactive group will be chosen such that it is capable of forming a covalent bond with members of the organic molecule library against which it is subsequently screened. In certain specific embodiments, the chemically reactive group is either a primary or secondary amine group and the library of organic compounds comprises aldehydes and/or ketones, wherein the chemically reactive group and the library members are capable of forming covalent bonds. In another specific embodiment, the chemically reactive group is either an aldehyde or ketone group and the library of organic compounds comprises primary and/or secondary amines, wherein the chemically reactive group and the library members are capable of forming covalent bonds. Using the techniques described above, chemically reactive groups may be introduced into specific predetermined sites on the biological target molecule or may be introduced randomly.

Once a biological target molecule that comprises a chemically reactive group of interest is obtained, the biological target molecule is then used to screen a library of organic compounds to identify those organic compounds that form a covalent bond with the chemically reactive group. It is expected that those members of the library of organic compounds that have the greatest relative affinity for the site on the polypeptide being assayed will be those that covalently bond to the chemically reactive functionality most abundantly. For example, it has been demonstrated that allosteric effects in a polypeptide can function to determine the reactivity of an organic compound for a reactive site on the polypeptide (see, e.g., Abraham et al., *Biochemistry* 34:15006–15020 (1995)). Thus, it is expected that by screening mixtures of two or more organic compounds against a chemically reactive group at a site of interest on a target biomolecule, those organic compounds having the highest non-covalent affinity for the site of interest will be capable of most efficiently forming covalent bonds with the chemically reactive group at that site. In this manner, one can determine which library members have the highest relative binding affinity for the site being tested, wherein that binding affinity is directly related to the ability of those compounds to form covalent bonds with the chemically reactive group at the site of interest.

As described above, the library of organic molecules and the chemically reactive group are chosen to be "compatible", i.e., chosen such that they are capable of reacting with one another to form a covalent bond. The library of organic compounds to be screened against the modified polypeptide of interest may be obtained in a variety of ways including, for example, through commercial and non-commercial sources, by synthesizing such compounds using standard chemical synthesis technology or combinatorial synthesis technology (see Gallop et al., *J. Med. Chem.* 37:1233–1251 (1994), Gordon et al., *J. Med. Chem.* 37:1385–1401 (1994), Czarnik and Ellman, *Acc. Chem. Res.* 29:112–170 (1996), Thompson and Ellman, *Chem. Rev.* 96:555–600 (1996), and Balkenhohl et al., *Angew. Chem. Int. Ed.* 35:2288–2337 (1996)) and by obtaining such compounds as degradation products from larger precursor compounds, e.g. known therapeutic drugs, large chemical molecules, and the like. Often the covalent interaction between the chemically reactive group and the library member will be exchangeable, thereby allowing one to identify small molecules that bind in the presence of those that do not. Also, exchangeable covalent bonds will be capable of being made non-exchangeable, thereby "trapping" the small organic ligand that is covalently bound to the target.

The "organic compounds" employed in the methods of the present invention will be, for the most part, small chemical molecules that will generally be less than about 2000 daltons in size, usually less than about 1500 daltons in size, more usually less than about 750 daltons in size, preferably less than about 500 daltons in size, often less than about 250 daltons in size and more often less than about 200 daltons in size, although organic molecules larger than 2000 daltons in size will also find use herein. Organic molecules that find use may be employed in the herein described method as originally obtained from a commercial or non-commercial source (for example, a large number of small organic chemical compounds are readily obtainable from commercial suppliers such as Aldrich Chemical Co., Milwaukee, Wis. and Sigma Chemical Co., St. Louis, Mo.) or may be obtained by chemical synthesis.

Organic molecule compounds that find use in the present invention include, for example, aldehydes, ketones, oximes, such as O-alkyl oximes, preferably O-methyl oximes, hydrazones, semicarbazones, carbazides, primary amines, secondary amines, such as N-methylamines, tertiary amines, such as N,N-dimethylamines, N-substituted hydrazines, hydrazides, alcohols, ethers, thiols, thioethers, thioesters, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, and the like, all of which have counterpart chemically reactive groups that allow covalent bond formation with the modified polypeptide of interest. In fact, virtually any small organic molecule that is capable of covalently bonding to a known chemically reactive functionality may find use in the present invention with the proviso that it is sufficiently soluble and stable in aqueous solutions to be tested for its ability to bind to the biological target molecule.

Various chemistries may be employed for forming a covalent bond between the chemically reactive group and a member of the organic molecule library including, for example, reductive aminations between aldehydes and ketones and amines (March, *Advanced Organic Chemistry*, John Wiley & Sons, New York, 4th edition, 1992, pp.898–900), alternative methods for preparing amines (March et al., supra, p.1276), reactions between aldehydes and ketones and hydrazine derivatives to give hydrazones and hydrazone derivatives such as semicarbazones (March et al., supra, pp.904–906), amide bond formation (March et al., supra, p.1275), formation of ureas (March et al., supra, p.1299), formation of thiocarbamates (March et al., supra, p.892), formation of carbamates (March et al., supra, p.1280), formation of sulfonamides (March et al., supra, p.1296), formation of thioethers (March et al., supra, p.1297), formation of disulfides (March et al., supra, p.1284), formation of ethers (March et al., supra, p.1285), formation of esters (March et al., supra, p.1281), additions to epoxides (March et al., supra, p.368), additions to aziridines (March et al., supra, p.368), formation of acetals and ketals (March et al., supra, p.1269), formation of carbonates (March et al., supra, p.392), formation of enamines (March et al., supra, p.1284), metathesis of alkenes (March et al., supra, pp.1146–1148 and Grubbs et al., *Acc. Chem. Res.* 28:446–452 (1995)), transition metal-catalyzed couplings of aryl halides and sulfonates with alkenes and acetylenes (e.g., Heck reactions) (March et at., supra, pp.717–178), the reaction of aryl halides and sulfonates with organometallic reagents (March et al., supra, p.662), such as organoboron (Miyaura et al., *Chem. Rev.,* 95:2457 (1995)), organotin, and organozinc reagents, formation of oxazolidines (Ede et al., *Tetrahedron Letts.* 38:7119–7122 (1997)), formation of thiazolidines (Patek et al., *Tetrahedron Letts.* 36:2227–2230

(1995)), amines linked through amidine groups by coupling amines through imidoesters (Davies et al., *Canadian J. Biochem.* 50:416–422 (1972)), and the like.

Libraries of organic compounds which find use herein will generally comprise at least 2 organic compounds, often at least about 25 different organic compounds, more often at least about 100 different organic compounds, usually at least about 300 different organic compounds, more usually at least about 500 different organic compounds, preferably at least about 1000 different organic compounds, more preferably at least about 2500 different organic compounds and most preferably at least about 5000 or more different organic compounds. Populations may be selected or constructed such that each individual molecule of the population may be spatially separated from the other molecules of the population (e.g., each member of the library is a separate microtiter well) or two or more members of the population may be combined if methods for deconvolution are readily available. The methods by which the populations of organic compounds are prepared will not be critical to the invention. Usually, each member of the organic molecule library will be of the same chemical class (i.e., all library members are aldehydes, all library members are primary amines, etc.), however, libraries of organic compounds may also contain molecules from two or more different chemical classes.

Reaction conditions for screening a library of organic compounds against a chemically reactive group-containing biological target molecule will be dependent upon the nature of the chemically reactive group and the chemical nature of the chosen library of organic compounds and can be determined by the skilled artisan in an empirical manner. For the step of screening a population of organic molecules to identify those that bind to a target polypeptide, it will be well within the skill level in the art to determine the concentration of the organic molecules to be employed in the binding assay. For the most part, the screening assays will employ concentrations of organic molecules ranging from about 0.1 $\mu$M to 50 mM, preferably from about 0.01 to 10 mM, although concentrations outside those ranges may also find use herein.

In a particularly preferred embodiment, the chemically reactive group that is linked to the biological target molecule and the library of organic molecules to be screened against the target molecule are chosen such that they are capable of reacting to form a Schiff base adduct. A Schiff base adduct is formed from the condensation of aldehydes or ketones with primary or secondary amines. Thus, in one embodiment of the present invention, the chemically reactive group is a primary or secondary amine group and the library of organic compounds against which the target molecule is screened comprises aldehyde and/or ketone compounds. In another preferred embodiment, the chemically reactive group is either an aldehyde or ketone group and the library of organic compounds against which the biological target molecule is screened comprises primary and/or secondary amines. Once a reversible Schiff base adduct is formed between the aldehyde or ketone group and the primary or secondary amine (an interaction that is relatively unstable and reversible), the imine bond created may optionally be reduced (i.e., made irreversible) by the addition of a reducing agent so as to stabilize the covalently bonded product of the reaction. Such allows one to identify small organic molecule ligands that bind to the target protein in the presence of those that do not. Reducing agents that find use for such purposes include, for example, sodium cyanoborohydride, sodium triacetoxyborohydride, cyanide, and the like, i.e., agents that would not be expected to disrupt any disulfide bonds present on the target biomolecule (see, e.g., Geoghegan et al., *J. Peptide and Protein Res.* 17(3): 345–352 (1981)).

Combining the biological target molecule of interest with one or more members of a library of organic compounds will result in the formation of a covalent bond between the chemically reactive group present on the target molecule and a member of the organic compound library. Once such a covalent bond is formed, one may identify the organic compound that bound in a number of ways. For example, in the case where the chemically reactive group was linked to the target biomolecule through a disulfide bond, one may liberate the organic compound from the target molecule by treatment of the covalently bound complex with an agent that disrupts the disulfide bond that was formed between the free thiol group of the target molecule of interest and the compound that comprises (1) a thiol functionality and (2) the chemically reactive group. For the most part, agents capable of disrupting the disulfide bond through which the covalently bound organic compound is linked to the target molecule of interest will be reducing agents such as, for example, dithiothreitol, dithioerythritol, β-mercaptoethanol, phosphines, sodium borohydride, and the like, preferably thiol-group containing reducing agents.

Once an organic compound that covalently bound to the chemically reactive group of the target molecule has been liberated from the complex by treatment with an agent that disrupts the disulfide bond through which the organic compound is linked, the identity of the actual organic compound that bound to the target molecule of interest is determined by a variety of means. For example, the well known technique of mass spectrometry may preferably be employed either alone or in combination with other means for detection for identifying the organic compound ligand that bound to the target of interest. Techniques employing mass spectrometry are well known in the art and have been employed for a variety of applications (see, e.g., Fitzgerald and Siuzdak, *Chemistry & Biology* 3:707–715 (1996), Chu et al., *J. Am. Chem. Soc.* 118:7827–7835 (1996), Siuzdak, *Proc. Natl. Acad. Sci USA* 91:11290–11297 (1994), Burlingame et al., *Anal. Chem.* 68:599R-651R (1996), Wu et al., *Chemistry & Biology* 4:653–657 (1997) and Loo et al., *Am. Reports Med. Chem.* 31:319–325 (1996)).

In other embodiments, subsequent to the covalent bonding of the library member to the chemically reactive group of the target molecule, the target molecule/organic compound conjugate may be directly subjected to mass spectrometry or may be fragmented and the fragments then subjected to mass spectrometry for identification of the organic compound that bound to the target molecule. The success of mass spectrometry analysis of the intact target protein/organic compound conjugate or fragments thereof will depend upon the nature of the target molecule and can be determined on an empirical basis.

In addition to the use of mass spectrometry, one may employ a variety of other techniques to identify the organic compound that covalently bound to the biological target molecule of interest. For example, one may employ various chromatographic techniques such as liquid chromatography, thin layer chromatography, and the like, for separation of the components of the reaction mixture so as to enhance the ability to identify the covalently bound organic molecule. Such chromatographic techniques may be employed in combination with mass spectrometry or separate from mass spectrometry. One may optionally couple a labeled probe (fluorescently, radioactively, or otherwise) to the liberated organic compound so as to facilitate its identification using any of the above techniques. Other techniques that may find use for identifying the organic compound that bound to the target biomolecule include, for example, nuclear magnetic resonance (NMR), capillary electrophoresis, X-ray crystallography, and the like, all of which will be well known by those skilled in the art.

Another embodiment of the present invention is directed to a method for identifying a ligand that binds to a biological target molecule of interest, wherein the method comprises employing the above described methods to identify two or more organic molecule ligands that bind to the target of interest and linking those two or more organic molecule ligands through a linker element to form a conjugate molecule that also binds to the target of interest. For the most part, the conjugate molecule that is comprised of two or more individual organic molecule ligands for the target molecule will bind to the target of interest with a lower dissociation constant than any of the individual components, although such is not a requirement of the invention. The individual organic molecule components of a conjugate molecule may bind to the same site or different sites on the target of interest and may be from the same or different chemical classes. By "same chemical class" is meant that each component of the conjugate is of the same chemical type, i.e., each are aldehydes, each are amines, etc.

Linker elements that find use for linking two or more organic molecule ligands to produce a conjugate molecule will be multifunctional, preferably bifunctional, cross-linking molecules that can function to covalently bond at least two organic molecules together via reactive functionalities possessed by those molecules. Linker elements will have at least two, and preferably only two, reactive functionalities that are available for bonding to at least two organic molecules, wherein those functionalities may appear anywhere on the linker, preferably at each end of the linker and wherein those functionalities may be the same or different depending upon whether the organic molecules to be linked have the same or different reactive functionalities. Linker elements that find use herein may be straight-chain, branched, aromatic, and the like, preferably straight chain, and will generally be at least about 2 atoms in length, more generally more than about 4 atoms in length, and often as many as about 12 or more atoms in length. Linker elements will generally comprise carbon atoms, either hydrogen saturated or unsaturated, and therefore, may comprise alkanes, alkenes or alkynes, and/or other heteroatoms including nitrogen, sulfur, oxygen, and the like, which may be unsubstituted or substituted, preferably with alkyl, alkoxyl, hydroxyalkyl or hydroxy groups. Linker elements that find use will be a varying lengths, thereby providing a means for optimizing the binding properties of a conjugate ligand compound prepared therefrom.

In yet other embodiments of the present invention, one may obtain a target molecule/organic molecule conjugate as described above and then "build off" of the first organic compound that covalently bound to the chemically reactive group of the target molecule. For example, the first organic compound that covalently bound to the target biomolecule may itself provide a chemically reactive group to which a second organic compound may covalently bond. As such, a target biomolecule/organic compound conjugate may be screened against a library of organic compound to identify a second organic compound capable of covalently bonding to a chemically reactive group on the first organic molecule. This process may be repeated in an iterative process to obtain progressively higher affinity organic molecules for binding to the target molecule. As described above, the first organic compound may itself possess a chemically reactive group that provides a site for bonding to a second organic molecule or, in the alternative, the first organic molecule may be modified (either chemically, by binding a compound comprising a chemically reactive group thereto, or otherwise) prior to screening against a second library of organic compounds.

Further details of the invention are illustrated in the following non-limiting examples.

EXPERIMENTAL

A plasmid containing the thymydilate synthase gene derived from *E. coli* will be mutated such that the five normally occurring cysteine residues are converted to serine residues using site-directed mutagenesis. At the same time, a single cysteine residue will be engineered into the enzyme active site. In one case, this could be the normally occurring catalytic cysteine (C146). In another case, this cysteine residue might take the place of an arginine residue (such as R127) which has been shown not to significantly affect the activity of the enzyme when it is mutated (Carreras and Santi, *Annu. Rev. Biochem.* 64:721–762 (1995)). One can make any number of different mutant proteins containing a single cysteine residue in various locations in and around the active site of the enzyme. These mutant proteins will be overexpressed and purified as previously described (Maley and Maley, *J. Biol. Chem.* 263:7620–7627 (1988)). Generally, the enzyme will be tested for substrate binding and, in the case of the C146 mutant, activity, to ensure that the mutations do not significantly perturb the structure of the protein. In all cases, the protein could be subjected to one or more of the following three treatments.

In the first case, the mutant protein will be reacted with one molar equivalent of a cysteamine/thionitrobenzoic acid mixed disulfide. This reagent would be prepared by reacting cysteamine (otherwise known as 2-aminoethanethiol) with a thiol activating agent such as 5,5'-dithio-bis(2-nitrobenzoic acid) (DTNB) and purifying the product using the standard techniques of organic chemistry. The protein would react with the reagent to form a new mixed disulfide in which the cysteine group on the protein is attached to the cysteamine moiety through a disulfide bond. The free primary amine group of the cysteamine would then be free to react with aldehydes.

In a typical experiment, individual libraries each consisting of a set of ten different aldehydes chosen to be of similar reactivity and structure will be mixed with the cysteamine-modified protein in aqueous buffered solution. Initial experiments will dictate the concentration of aldehydes used; at first, a wide range of different concentrations will be tested. During this time the aldehyde functionality of individual library members will react with the primary amine group of the protein-bound-cysteamine to yield an imine. Because this reaction is reversible, equilibrium will favor imine formation with the library member that had the highest intrinsic affinity for the active site of the protein. After allowing the libraries of aldehydes to react with the protein for varying lengths of time, the solution will be treated with sodium cyanoborohydride to reduce the imines to secondary amines. The protein-cysteamine-compound complex will then be purified away from the unreacted members of the library by using dialysis, chromatography, precipitation, or other methods. Next, the protein will be treated with a disulfide-reducing agent such as dithiothreitol (DTT) or tris-(2-carboxyethyl)-phosphine (TCEP), thereby cleaving the disulfide bond and releasing the captured library member (s) from the protein. These will then be analyzed directly using mass-spectrometry (MS), or they will first be conjugated to a fluorescent dye (such as fluorescein by reaction with fluorescein-maleimide) through their thiol moieties and then analyzed by a combination of chromatography (HPLC or CE) and MS. The later method will allow quantitation of the released library members, and will facilitate analysis if more than a single library member bound to the cysteamine-portion of the protein. It should be noted that the initial library can contain more or fewer than ten compounds; the ideal number being determined empirically, and will probably vary with different combinations of mutants and libraries.

A second methodology will involve reacting the single-cysteine-containing mutant protein with a thioglycerol/thionitrobenzoic acid mixed disulfide, which will be synthesized analogously to the cysteamine/thionitrobenzoic acid mixed disulfide described above. Once the thioglycerol is attached to the protein through a disulfide bond, the modified protein will be treated with a 15 mM sodium periodate solution for 15 minutes at room temperature (Acharya and Manjula, *Biochemistry* 26:3524–3530 (1987)) so as to oxidize the glycol portion to an aldehyde. This aldehyde-containing protein will then be reacted with libraries consisting of pools of primary or secondary amines, and the rest of the procedure would be as described above.

A variation on this second methodology will involve using specially constructed libraries of amines that also contained the glycol functionality. After reacting these libraries with the protein and reducing the resulting imines to secondary amines, the proteins will be treated a second time with sodium periodate to oxidize the newly introduced glycol to an aldehyde. The protein-compound-aldehyde will then be reacted with a second amine-containing library and subsequently reduced with sodium cyanoborohydride. In principle, this process could be repeated several times so as to actually build an organic molecule within the active site of the protein. This is similar to the method of Huc and Lehn (Huc and Lehn, *Proc. Natl. Acad. Sci. USA* 94:2106–2110 (1997)), but with the significant advantage that the molecule is built selectively into a specified site of interest. Another advantage is that it is a linear, stepwise process, where we have control over each individual step.

Another variation on this second methodology is made possible by the fact that after reduction of the imine a secondary amine is formed, and this can in principle be reacted with a library of aldehydes. In practice, primary amine libraries will be screened against the original aldehyde-containing protein target, and the amine that binds most tightly will be identified. This amine alone will then be conjugated to the aldehyde-containing protein and reduced to form a secondary amine. In other words, a new target protein will be prepared, consisting of the original target protein coupled to the amine selected from the first library and containing a secondary amine. This new target protein will then be reacted with a library of aldehydes, and the aldehyde that binds most tightly will be identified. There are several advantages to this methodology. First, as described in the preceding paragraph, it is a stepwise approach, where each step can be optimized for speed and accuracy. Second, two separate libraries are screened so as to maximize the diversity with a minimum degree of effort. For example, if the amine library and the aldehyde library each contain a mere 1000 members, then although there are one million possible combinations, in practice only 1000 of these need to be sampled in order to identify the tightest-binder (i.e., the single tightest-binding amine pre-bound to the protein and screened against the library of 1000 aldehydes). Finally, this variation requires only simple primary amines and aldehydes or ketones, of which a large number are readily available. It should be noted that a similar approach can be used for the first (cysteamine-based) methodology, as that method also has the potential to generate a secondary amine.

A third methodology will involve reacting the single-cysteine-containing mutant proteins with libraries of disulfides. Because disulfide formation, like imine formation, is reversible, the process should be equilibrium-driven, such that library members that have the highest inherent affinity for the active site will tend to form disulfide bonds with the protein most often. The thiol-disulfide exchange will be further promoted by adding various concentrations of reduced and oxidized 2-mercaptoethanol so as to fine tune the reactivity. The protein will be purified away from the unbound library members and analyzed as described in the first method.

The foregoing description details specific methods which can be employed to practice the present invention. Having detailed such specific methods, those skilled in the art will well enough know how to devise alternative reliable methods at arriving at the same information in using the fruits of the present invention. Thus, however, detailed the foregoing may appear in text, it should not be construed as limiting the overall scope thereof; rather, the ambit of the present invention is to be determined only by the lawful construction of the appended claims. All documents cited herein are expressly incorporated by reference.

What is claimed is:

1. A process comprising
   (a) screening a library of small organic compounds, less than about 2000 daltons in size, with a target protein-ligand conjugate formed by the covalent bonding of a target protein comprising a first reactive functionality with a ligand that (1) comprises less than about 20 carbon atoms; (2) has affinity for interacting with a particular site on the target protein, (3) comprises a second reactive functionality and (4) comprises a free chemically reactive group, wherein the second reactive functionality of the ligand reacts with the first reactive functionality of the target protein to form a first covalent bond such that the ligand in the target protein-ligand conjugate contains a free chemically reactive group, in aqueous solution, under conditions wherein at least one member of the library forms a second covalent bond with said free chemically reactive group in the target protein-ligand conjugate, and
   (b) determining the identity of a small organic compound that binds covalently to the free chemically reactive group of the target protein-ligand conjugate.

2. The process of claim 1 wherein the second covalent bond is a disulfide bond.

3. The process of claim 1 wherein the free chemically reactive group is a thiol.

4. The process of claim 1 wherein each member of the library of small organic compounds comprises thiols or disulfides.

5. The process of claim 4 wherein each member of the library further contains a group selected from amides, secondary amides, disulfides and carbamates.

6. The process of claim 1 wherein the identifying step comprises using mass spectrometry.

7. The process of claim 6 wherein mass spectrometry is used to measure the mass of complex formed by the small organic compound covalently bound to the target protein-ligand conjugate.

8. The process of claim 7 wherein the complex is first fragmented prior to subjecting it to mass spectrometry.

9. The process of claim 8 comprising liberating or releasing the small organic compound from the complex prior to subjecting the small organic molecule to mass spectrometry.

10. The process of claim 9 wherein the liberating step comprises treating the conjugate with an agent that disrupts the disulfide bond through which the small organic compound forms a complex with the target protein-ligand conjugate.

11. The process of claim 10 wherein the agent is selected from borohydride or a phosphine.

12. The process of claim 10 further comprising coupling the liberated small organic compound to a labeled probe that facilitates identification of the compound by mass spectrometry.

13. The process of claim 1 wherein the target protein is selected from enzymes, proteases, kinases, phosphatases (dephosphorylases), cytokine receptors, hormones, interleukins, tyrosine kinase receptors, TNF, mdm2, chemokines and their receptors, signal transduction molecules and transcription factors.

14. The process of claim 11 wherein said agent is tris-(2-carboxyethyl)-phosphine (TECP).

15. The process of claim 1 wherein the first reactive functionality is an -SH group, masked -SH group, or activated -SH group.

16. The process of claim 15 wherein said -SH group, masked -SH group, or activated -SH group is associated with a cysteine residue of said target protein.

* * * * *